United States Patent [19]

Denis et al.

[11] Patent Number: 5,449,386
[45] Date of Patent: Sep. 12, 1995

[54] AMINE PHOSPHATES HAVING A TERMINAL CYCLIC IMIDE

[75] Inventors: Jacques Denis, Charbonnieres les Bains; Jacques Garapon, Lyons; Alain Forestiere, Vernaison; Gérard Leleu; Despina Vassilakis, both of Lyons; Robert Léger, Taluyers, all of France

[73] Assignees: Institut Francais du Petrole, Rueil Malmaison; Elf Antar France, Paris La Defense, both of France

[21] Appl. No.: 134,835

[22] Filed: Oct. 12, 1993

[30] Foreign Application Priority Data

Oct. 9, 1992 [FR] France .................. 92 12277
Dec. 18, 1992 [FR] France .................. 92 15441

[51] Int. Cl.$^6$ .............................................. C10L 1/26
[52] U.S. Cl. .................................. 44/347; 548/413; 548/414; 548/415
[58] Field of Search .................. 548/413, 415; 44/347

[56] References Cited

U.S. PATENT DOCUMENTS

| | | | |
|---|---|---|---|
| 2,706,194 | 4/1955 | Morris et al. | 548/413 |
| 3,502,677 | 3/1970 | LeSuer | 548/413 |
| 3,547,946 | 12/1970 | Lorenz et al. | 548/413 |
| 3,654,307 | 4/1972 | Jamison | 548/413 |
| 3,795,495 | 3/1974 | Howland et al. | 44/58 |
| 3,849,440 | 11/1974 | Golborn et al. | 548/413 |
| 3,865,740 | 2/1975 | Goldschmidt | 548/413 |
| 3,960,812 | 6/1976 | Renner et al. | 548/413 |
| 3,980,448 | 9/1976 | Haemmerle et al. | 44/63 |
| 4,014,803 | 3/1977 | Romine | 252/32.7 R |
| 4,128,558 | 12/1978 | Hendricks et al. | 548/413 |
| 4,234,435 | 11/1980 | Meinhardt et al. | 252/51.5 A |
| 5,130,304 | 7/1992 | Binderup et al. | 548/413 |

FOREIGN PATENT DOCUMENTS

| | | |
|---|---|---|
| 0071513 | 2/1983 | European Pat. Off. . |
| 0465042 | 1/1992 | European Pat. Off. . |
| 1231950 | 10/1960 | France . |
| 2130802 | 10/1972 | France . |
| 2307032 | 11/1976 | France . |
| 2426730 | 12/1979 | France . |
| 2531448 | 2/1984 | France . |
| WO83/03616 | 10/1983 | WIPO . |

OTHER PUBLICATIONS

Chemical Abstracts, vol. 90, 1979, Abstract No. 106667w. (Month Unknown).

*Primary Examiner*—Ellen M. McAvoy
*Attorney, Agent, or Firm*—Millen, White, Zelano, & Branigan

[57] ABSTRACT

Amine phosphate having a terminal imide cycle resulting from the reaction, under formation conditions for an amine salt, of at least one phosphate complying with the general formula (I):

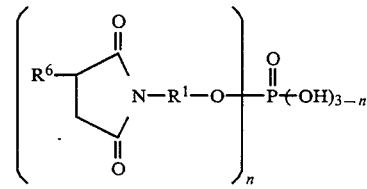

in which n is equal to 1 or 2, $R^1$ is a divalent hydrocarbon group having 1 to 32 carbon atoms, $R^6$ stands for a hydrogen atom or a hydrocarbon group normally having 1 to 200 carbon atoms, with at least one amine. Preparation process in accordance with standard methods and use of these compounds as additives in fuels for engines, if appropriate in formulations containing a second constituent consisting of at least one product chosen from among the germination additives of paraffins, whereby said formulations can also contain at least one paraffin crystal growth inhibiting product.

23 Claims, No Drawings

AMINE PHOSPHATES HAVING A TERMINAL CYCLIC IMIDE

BACKGROUND OF THE INVENTION

The present invention relates to phosphates of amines having at least one terminal imide cycle, a process for the preparation of these compounds and their uses as additives permitting, during the cooling of the middle distillates of hydrocarbons containing paraffins (fuel oils, gas oils) the slowing down of the sedimentation of these paraffins.

In winter, deposits may form on tanks containing non-dewaxed petroleum products such as middle distillates and in particular domestic fuels and gas oils. These deposits are due to the crystallization and sedimentation of paraffins, which become insoluble when the temperature drops below the cloud point (in France $-5°$ C. for gas oils and $+2°$ C. for domestic fuels).

The lower the temperature the greater the crystallization. It consists of the joining of paraffin molecules along their major axis, which leads to a growth in the form of very fine platelets, which can agglomerate with one another. The sedimentation of these paraffin crystals is dependent on the one hand on their size and their morphology, which are a function of the composition of the fraction and the cooling rate, and on the other of the fluidity of the medium.

Sedimentation has a prejudicial effect both in storage containers and in vehicle tanks, because the orifice of the suction pipes is located in the bottom of the tanks, where the product is concentrated in solid paraffin form. This product sucked in at the start of pumping may rapidly clog the filters of the supply circuit, which hold back the crystallized paraffins.

SUMMARY OF THE INVENTION

The present invention relates to ionic compounds liable to be fixed on the incipient crystals of paraffins, preventing the growth and agglomeration thereof and consequently keeping the suspension homogeneous when the temperature continues to drop. The invention also relates to middle petroleum distillate compositions incorporating a major proportion of a middle petroleum distillate and a minor proportion, sufficient to limit the sedimentation rate of the paraffins contained in said middle distillate, of at least one additive chosen from within the group of amine phosphates having a terminal imide cycle and as defined hereinafter.

The petroleum distillates to which the present invention relates consist of middle distillates (fuel oils, gas oils) containing paraffins with a distillation range (standard ASTM D 86-67) between 150° and 450° C., especially those gas oils having a distillation range between an initial temperature of 160° to 190° C. and a final temperature between 350° and 390° C.

The amine phosphates having a terminal imide cycle according to the present invention are compounds obtained by the reaction, under formation conditions of an amine salt, of at least one phosphate complying with the general formula (I) given hereinafter and at least one amine complying with the general formula (II) or (III) given hereinafter. The present invention also relates to phosphates of general formula (I), more particularly as intermediates for the synthesis of the amine phosphates according to the present invention. These phosphates comply with the general formula (I):

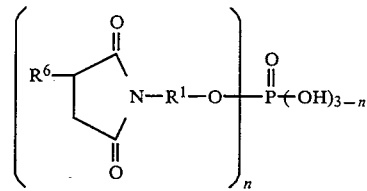

in which n is equal to 1 or 2, $R^1$ is a divalent hydrocarbon group having 1 to 32 carbon atoms, $R^6$ represents a hydrogen atom or a hydrocarbon group normally having 1 to 200 carbon atoms. Usually $R^1$ is a straight or branched, divalent, saturated aliphatic group, which usually has 1 to 18 and preferably 2 to 18 carbon atoms, or an aromatic group, optionally incorporating substituents, such as e.g. alkyl groups and in particular lower alkyl groups. This aromatic group usually has 6 to 24 and preferably 6 to 18 carbon atoms. The said $R^1$ group is preferably a divalent, saturated aliphatic group and usually has 2 to 16 atoms and is either linear, or has branches in the form of lower alkyl groups, such as methyl, ethyl, propyl or butyl groups and preferably methyl or ethyl groups.

The amines used for forming the amine phosphates of the present invention comply with the general formula (II) or the general formula (III):

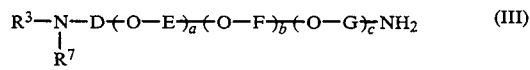

in which $R^3$, $R^4$ and $R^5$, which can be the same or different in each case represent a hydrogen atom or a hydrocarbon group having 1 to 60 and preferably 1 to 48 carbon atoms, Z is chosen from among the —O— and —$NR^7$— groups, in which $R^7$ represents a hydrogen atom or a hydrocarbon group having 1 to 60 and preferably 1 to 48 carbon atoms, $R^3$ and $R^7$ being able to form together with the nitrogen atom to which they are linked a heterocycle, each of the $R^2$ independently representing a hydrogen atom or a hydrocarbon group having 1 to 4 carbon atoms. When Z is —$NR^7$—, p is an integer equal to or higher than 2 and preferably between 2 and 10 and m is zero or an integer between 1 and 10. When Z is —O—, p is an integer equal to or higher than 1, preferably between 1 and 10 and m is an integer from 1 to 10. D, E, F and G, which can be the same or different, in each case represent a divalent hydrocarbon group having 2 to 6 carbon atoms, a is an integer from 1 to 60, b and c, which can be the same or different, are in each case zero or an integer from 1 to 50 and the sum a+b+c is an integer from 1 to 60.

Among the most frequently used amines reference can be made to those of formula (II) in which m is equal to zero. These monoamines comply with the general formula $R^3R^4R^7N$ and frequently use is made of those in which $R^4$ and $R^7$ in each case represent a hydrogen atom and $R^3$ an alkyl group having 1 to 32 carbon atoms. As examples of these primary monoamines, reference can be made to methyl amine, ethyl amine, propyl amine, butyl amine, pentyl amine, hexyl amine, heptyl amine, octyl amine, nonyl amine, decyl amine, dodecyl amine, tetradecyl amine, hexadecyl amine, octadecyl amine, eicosyl amine and docosyl amine. It is also possible to use a mixture of primary monoamines. Use is frequently made of secondary monoamines of formula $R^3R^4NH$, in which $R^3$ and $R^4$, which can be the same or different, in each case represent an alkyl group having 1 to 32 carbon atoms or a mixture of secondary monoamines, such as e.g. fatty amine fractions of formula $R^3R^4NH$, whose groups $R^3$ and $R^4$ are aliphatic hydrocarbon radicals in the $C_8, C_{10}, C_{12}, C_{14}, C_{16}, C_{18}, C_{20}$ and $C_{22}$ positions, in the approximate molar proportions given in the following table I.

It is also possible to use polyamines of formula (II), in which $R^3$ is a hydrogen atom or a hydrocarbon group having 1 to 32 carbon atoms, Z is preferably a $—NR^7—$ group, in which $R^7$ preferably stands for a hydrogen atom or a hydrocarbon group having 1 to 32 carbon atoms, each of the $R^2$ independently preferably representing a hydrogen atom or a methyl group, p is an integer from 2 to 4 and when Z is a $—NR^7—$, m is preferably an integer from 1 to 5.

Among the compounds of general formula (II), it is possible to use those in which Z is $—NR^7—$, $R^3, R^2$ and $R^7$ each represent a hydrogen atom, p is equal to 2 and m is an integer from 1 to 5, or those in which $R^3$ represents a hydrocarbon group preferably having 5 to 24 carbon atoms, Z represents a $—NR^7—$ group, in which $R^7$ is a hydrogen atom, $R^2$ represents a hydrogen atom, p is an integer from 2 to 4, preferably 3, and m is an integer from 1 to 5, preferably 1.

The hydrocarbon groups $R^3$ and $R^7$ are normally straight or branched, alkenyl, alkyl, aryl, aryl-alkyl (aralkyl), alkyl-aryl (alkaryl) or cycloaliphatic groups. The groups $R^3$ and $R^7$ are preferably straight or branched, alkyl or alkenyl groups. The hydrocarbon group $R^2$ is normally a preferably straight alkyl group and is e.g. a methyl, ethyl, n-propyl or n-butyl group.

As specific compounds reference can be made to ethylene diamine, propylene diamine, triethylene tetramine, tripropylene tetramine, tetraethylene pentamine, trimethylene diamine, hexamethylene diamine, 2,2,4 and 2,4,4-trimethyl hexamethylene diamine, di(trimethylene)triamine, N-alkyl-1,3-diamino propane, e.g. N-1,3-dodecyldiaminopropane, N-1,3-tetradecyldiaminopropane, N-1,3-hexadecyldiaminopropane, N-1,3-octadecyldiaminopropane, N-1,3-eicosyldiaminopropane and N-1,3-docosyldiaminopropane. Reference can also be made to N-alkyl dipropylene triamines, e.g. N-hexadecyl dipropylene triamine, N-octadecyl dipropylene triamine, N-eicosyl dipropylene triamine and N-docosyl dipropylene triamine. Reference can also be made to N-1,3-alkenyldiaminopropane and N-alkenyl dipropylene triamines, e.g. N-1,3octadecenyl diaminopropane, N-1,3-hexadecenyl diaminopropane, N-1,3-dodecylenyl diaminopropane, N-1,3-octadecadienyl diaminopropane and N-1,3-docosenyl diaminopropane. As examples of N,N-disubstituted diamines reference can be made to N,N-diethyl-1,2-diaminoethane, N,N-diisopropyl-1,2-diaminoethane, N,N-dibutyl-1,2-diaminoethane, N,N-diethyl-1,4-diaminobutane, N,N-dimethyl-1,3-diaminopropane, N,N-diethyl-1,3-diaminopropane, N,N-dioctyl-1,3-diaminopropane, N,N-didecyl-1,3-diaminopropane, N,N-didodecyl-1,3-diaminopropane, N,N-ditetradecyl-1,3-diaminopropane, N,N-dihexadecyl-1,3-diaminopropane, N,N-dioctadecyl-1,3-diaminopropane, N,N-didodecyldipropylene triamine, N,N-ditetradecyldipropylene triamine, N,N-dihexadecyldipropylene triamine, N,N-dioctadecyldipropylene triamine, N-methyl, N-butyl, 1,2-diaminoethane, N-methyl-N-octyl-1,2-diaminoethane, N-ethyl, N-octyl-1,2-diaminoethane, N-methyl-N-decyl-1,2-diaminoethane, N-methyl-N-dodecyl-1,3-diaminopropane, N-methyl-N-hexadecyl-1,3-diaminopropane and N-ethyl-N-octadecyl-1,3-diaminopropane.

As examples of ether amines reference can be made to 2-methoxyethylamine, 3-methoxypropylamine, 4-methoxybutylamine, 3-ethoxypropylamine, 3-octyloxypropylamine, 3-decyloxypropylamine, 3-hexadecyloxypropylamine, 3-eicosyloxypropylamine, 3-docosyloxypropylamine, N-(3-octyloxypropyl)-1,3-diaminopropane, N-(3-decyloxypropyl)-1,3-diaminopropane, (2,4,6-trimethyldecyl) 3-oxypropylamine, N-[(2,4,6-trimethyldecyl)3-oxypropyl]1,3-diaminopropane, di-(2-methoxyethyl)-amine, di-(3-methoxy n-propyl)amine, di-(2-methoxy 2-methyl-ethyl)-amine, di-(3-ethoxy-n-propyl)-amine, di-(n-3-propoxy-n-propyl)-amine, di-(n-3-butoxy-n-propyl)-amine, di-(n-3-pentoxy-n-propyl)-amine, di-(n-3-hexyloxy-n-propyl)-amine, di-(n-3-octyloxy-n-propyl)-amine, di-(n-3-nonyloxy-n-propyl)-amine and di-(n-3-decyloxy-n-propyl)-amine.

It must be understood that it is possible to use as the amine compound one or more compounds complying with formula (II) and/or (III). As specific examples for the mixing of compounds complying with formula (II) reference can be made to fatty diamine fractions complying with the formula $R^3—NH—(—CH_2—)_3—NH_2$, whereof the $R^3$ groups are aliphatic hydrocarbon radicals in the $C_8 C_{10} C_{12} C_{14}, C_{16}, C_{18}, C_{20}$ and $C_{22}$ positions, in the approximate molar ratios given in the following table I.

TABLE I

| Alkyl chains Fraction | $C_8$ | $C_{10}$ | $C_{12}$ | $C_{14}$ | $C_{16}$ | $C_{18}$ | $C_{18-1}$* | $C_{20}$ | $C_{22}$ |
|---|---|---|---|---|---|---|---|---|---|
| A | 0% | 0% | 0% | 1% | 28% | 71% | 0% | 0% | 0% |
| B | 0% | 0% | 0% | 1% | 5% | 42% | 0% | 12% | 40% |
| C | 3% | 6% | 56% | 18% | 10% | 2% | 5% | 0% | 0% |
| D | 0% | 0% | 0% | 0% | 16% | 4,9% | 79,1% | 0% | 0% |
| E | 0% | 0% | 0% | 2,3% | 31,8% | 24,2% | 39% | 2,7% | 0% |

*$C_{18-1}$ chain having an ethylene unsaturation.

The polyamines of formula (III) used are usually those in which $R^3$ and $R^7$ in each case represent a hydrogen atom, D, E, F and G, which can be the same or different, in each case represent an alkylene group having 2 to 4 carbon atoms, e.g. ethylene, trimethylene, methyl ethylene, tetramethylene, methyl trimethylene 1-methyl trimethylene and 2-methyl trimethylene, a is an integer from 1 to 60 and b and c are equal to zero, or a is an integer from 1 to 59, c is zero or an integer such that the sum a+c is 1 to 59 and b is an integer from 1 to 50, with in each case the sum a+b+c equal to an integer from 1 to 60.

As specific compounds of formula (III) reference can be made to those complying with the formulas:

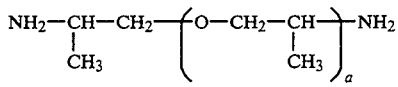

in which a is 2, 3, 5, 6 or approximately 33 and

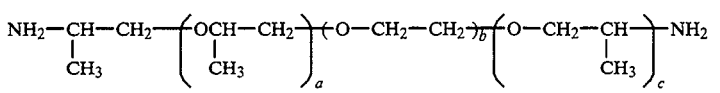

in which b is approximately equal to 8, 9, 15, 16 or 40 and a+c is approximately 2 or 3.

These products are in particular marketed by Texaco Chemical under the name Jeffamine EDR 148 for the product of formula (III1) in which a=2, Jeffamine D-230 for a product of formula (III2) of number average molecular weight 230, Jeffamine D-400 for a product of formula (III2) of number average molecular weight 400, Jeffamine D-2000 for a product of formula (III2) of number average molecular weight 2000, Jeffamine ED-600 for a product of formula (III3) of number average molecular weight 600, Jeffamine ED-900 for a product of formula (III3) of number average molecular weight 900 and Jeffamine ED-2001 for a product of formula (III3) of number average molecular weight 2000.

The phosphates of general formula (I) are compounds which can be prepared by any known method. These phosphates can in particular be obtained by reacting the phosphoric anhydride of formula $P_2O_5$ on an imide-alcohol of general formula (IV):

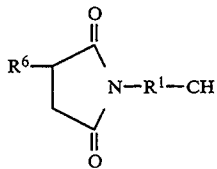

in which $R^1$ and $R^7$ have the definitions given hereinbefore. This imide-alcohol of general formula (IV) can be obtained by any known method. In particular, this compound results from the reaction, under the standard conditions for the formation of an imide cycle, an acid, a light alkyl semi-ester of said acid (methyl, ethyl, propyl or butyl semi-ester) or preferably a succinic anhydride of formula (V):

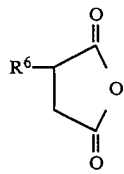

in which $R^6$ has the definition given hereinbefore, with an aminoalcohol of formula $HO—R^1—NH_2$ having a primary amine function and a preferably primary or secondary alcohol function and most usually a primary alcohol function. Conventionally said succinic compound has a number average molecular weight of approximately 100 to 3000, preferably 200 to 2000 and most usually 500 to 1500. These succinic derivatives are widely described in the prior art and are e.g. obtained by the action of at least one alpha olefin or a chlorinated hydrocarbon on maleic acid or anhydride. The alpha olefin or chlorinated hydrocarbon used in this synthesis can be straight or branched and normally have 10 to 150, preferably 15 to 80 and most usually 20 to 75 carbon atoms in their molecule. This olefin can also be an oligomer, e.g. a dimer, a trimer or a tetramer, or a polymer of a lower olefin, e.g. having 2 to 10 carbon atoms, such as ethylene, propylene, n-1-butene, isobutene, n-1-hexene, n-1-octene, 2-methyl-1-heptene or 2-methyl-5-propyl-1-hexene. It is possible to use mixtures of olefins or mixtures of chlorinated hydrocarbons.

As examples of the succinic anhydrides used reference can be made to succinic, methyl succinic, ethyl succinic, propyl succinic, n-hexyl succinic, n-octadecenyl succinic, dodecenyl succinic, n-tetradecyl succinic and polyisobutenyl succinic anhydrides the latter frequently being called PIBSA and having a number average molecular weight as defined hereinbefore.

As examples of the aminoalcohol used reference can be made to monoethanol amine, 1-amino-3-propanol, 1-amino-2-propanol, 1-amino-4-butanol, 1-amino-2-butanol, 1-amino-5-pentanol, 1-amino-6-hexanol, 1-amino-7-heptanol, 1-amino-8-octanol, 1-amino-10-decanol, 1-amino-11-undecanol, 1-amino-13-tridecanol, 1-amino-14-tetradecanol, 1-amino-16-hexadecanol, 2-amino-2-methyl-1-propanol, 2-amino-1-butanol and 2-amino-1-pentanol.

The amine phosphates according to the present invention can consequently be obtained by a preparation process having the following stages:

a) at least one aminoalcohol of formula $HO—R^1—NH_2$ is reacted with at least one succinic derivative and preferably a succinic anhydride of formula (V), at a temperature of approximately 30° C. to approximately 250° C., under conditions for the formation of the imide cycle and the elimination of the volatile products formed (water or alcohol). Usually the reaction is performed at a temperature of approximately 120° C. to approximately 200° C. with a molar ratio of aminoalcohol to succinic derivative of approximately 0.9:1 to approximately 1.2:1 and preferably approximately 1:1. This reaction can be performed in the absence of any solvent and preferably use is made of a solvent having a boiling point normally between 30° and 250° C. and usually between 65° and 210° C. This solvent is conventionally chosen so as to be able to permit the elimination of the water or alcohol formed during the imide cycle formation reaction. More particularly use is made of a solvent permitting the elimination of the water in the form of a water-solvent azeotrope. Conventionally use is made of an organic solvent such as e.g. an aromatic or naphtheno-aromatic hydrocarbon. More particularly, it is possible to use benzene, toluene, xylenes, ethyl benzene or a hydrocarbon fraction such as e.g. the commercial fraction Solvesso 150 (190°–209° C.) containing 99% by weight of aromatic compounds. It is possible to use mixtures of solvents, e.g. a mixture of xylenes. In practice, stage a) can be performed in the following way. Gradually the aminoalcohol is introduced into a reactor containing the dicarboxylic compound and whilst maintaining the temperature at between 30° and 80° C. The temperature is then raised to 120° to 200° C. whilst eliminating the volatile products formed (water or alcohols) either by entrainment with an inert gas flow, or by azeotropic distillation with the chosen solvent. The dry matter concentration is e.g. 40 to 70%, usually close to 50 to 60%. After adding the reagents, the reaction lasts e.g. between 1 and 8 hours and preferably between 3 and 6 hours.

b) Either the imide-alcohol of general formula (IV) obtained in stage a) diluted in a liquid (preferably a solvent) and preferably in one of those usable during stage a), or optionally after adjusting the dry matter concentration, e.g. to approximately 50% by weight, the imide-alcohol solution obtained in stage a) is progressively contacted with a suspension of phosphoric anhydride in a liquid, which is preferably the same as that in which the imide-alcohol is diluted. Contact takes place under conventional phosphate formation conditions. This formation of phosphates of general formula (I) takes place conventionally at a temperature of approximately 30° C. to approximately 120° C. The reaction is normally complete after approximately 30 minutes to approximately 2 hours. Although it is possible to use an excess of one or other of these compounds with respect to stoichiometry, normally preference is given to being close to said stoichiometry, i.e. reacting approximately 1 mole of phosphoric anhydride for 3 moles of imide-alcohol, which obviates having to eliminate the excess of one or other of these compounds. This usually leads to a mixture of phosphates mainly containing a phosphate having two free hydroxyl groups and a phosphate having one free hydroxyl group.

c) To the liquid containing the phosphate of general formula (I), or more usually a phosphate mixture of general formula (I) obtained in stage b), is slowly added at least one amine of general formula (II) and/or (III), preferably diluted in a liquid, which is generally the same as that used in stage b). This addition takes place under conventional amine salt formation conditions. This formation of the amine phosphate or phosphates normally takes place at a temperature of approximately 25° to approximately 100° C. The reaction is normally completed after approximately 30 minutes to approximately 2 hours. Although it is possible to use an excess of one or other of the compounds with respect to stoichiometry, preference is normally given to being close to said stoichiometry, i.e. reacting approximately one amine function per free hydroxyl function of the phosphate or phosphates, which makes it unnecessary to eliminate the excess of one or other of these compounds.

The compounds according to the present invention are more particularly usable as additives for engine fuel and more particularly as antisedimentation additives for engine fuel containing paraffins. Among these compounds, in connection with their use as additives for slowing down the decanting of paraffins in middle petroleum distillates (particularly gas oils), use is normally made of those in which the $R^6$ group has at least 6 and preferably at least 8 and most usually at least 10 or even at least 12 carbon atoms. The $R^6$ group is preferably a straight or branched, aliphatic group. When $R^6$ is a branched, aliphatic group, the branches are lower alkyl groups (methyl, ethyl, propyl or butyl and usually methyl or ethyl groups). Preferably, the $R^6$ group has a carbon chain with a straight portion having at least 6 carbon atoms.

Although the action mechanism of these additives on the sedimentation rate of paraffin crystals in middle distillates has not been clearly explained, there is a marked slowing down of the decanting of paraffins in middle distillates treated by these additives, when they are added in concentrations e.g. between 10 and 10,000 grammes per tonne (g/t) of middle distillate. The preferred concentrations are 50 to 5,000 g/t and most usually 100 to 2,000 g/t.

The present invention also relates to compositions having, by weight, a major proportion of an engine fuel containing paraffins and a minor proportion, adequate for slowing down the decanting of these paraffins during the cooling of said compositions, of at least one compound according to the present invention, as described hereinbefore or as prepared hereinafter. These compositions usually incorporate at least one compound according to the invention in the proportions mentioned hereinbefore. As examples of fuels which can contain at least one compound according to the present invention, reference can be made to gas oils or diesel fuels, such as those as defined in Standard ASTM D-975. These fuels can also contain other additives, such as antifreeze additives, anticorrosion additives and additives which are more specifically of the detergent type. In the additive concentration range of 10 to 10,000 g/t, it is possible to observe a reduction in the proportion of sedimented paraffins of up to 100% under the test conditions described hereinafter.

In order to formulate the middle distillate compositions according to the invention, it is possible to add the additives directly to the middle distillate by a simple mixing operation.

However, it is often advantageous to introduce them in the form of "mother solutions" prepared beforehand in the aforementioned solvents. The "mother solutions" can contain e.g. 20 to 60% and more usually approximately 50% by weight of additives.

The present invention also relates to additive formulations for fuels containing paraffins, incorporating at least one constituent (A) and at least one constituent (B), said constituent (A) consisting of at least one amine phosphate and said constituent (B) consisting of at least one product chosen from within the group formed by paraffin germination additives. It also relates to the use of these formulations as a composition permitting, during the cooling of middle hydrocarbon distillates containing paraffins (e.g. fuel oils or gas oils), to slow down the decanting of these paraffins, reduce the filterability temperature limit (FTL) and improve the operability temperature limit.

The sedimentation of paraffin crystals is dependent on the one hand on their size and morphology, which are a function of the composition of the fraction and the cooling rate, and on the other hand the fluidity of the medium. This fluidity can e.g. be increased with the aid of products known to the expert as additives improving the pour point. However, the use of pour point improving additives suffers from the major disadvantage of speeding up the sedimentation of the paraffins.

The present invention relates to formulations containing at least one paraffin germination additive and at least one ionic compound which can be fixed to the incipient paraffin crystals, preventing them from growing and agglomerating and consequently maintaining the suspension homogeneous when the temperature continues to drop. In other words, these formulations in particular make it possible to limit the sedimentation rate of paraffins contained in the middle distillate. In the preferred embodiment of the present invention, said formulations also contain at least one additive chosen from within the group formed by paraffin crystal growth inhibiting products. In this preferred form, said formulations have the advantage of making it possible to reach a lower filterability temperature limit than with the known additives, whilst also having a lower operability temperature limit.

The filterability temperature limit, in the sense of the present description, means the lowest temperature as from which, under a chosen test pressure, the filter used is completely clogged and the hydrocarbon flow passing through said filter becomes zero. The operability temperature limit is used, in the present description, to mean the lowest temperature as from which it becomes impossible to make an engine operate with the aid of the fuel, to which additives may or may not have been added, maintained in the supply circuit at a fixed temperature.

In the additive formulations for fuels containing paraffins according to the present invention, the constituent (A) consists of at least one amine phosphate having an imide cycle as defined hereinbefore.

The constituent (B) is preferably chosen from within the group formed by copolymers of lower olefins having 2 to 12 and preferably 2 to 4 carbon atoms and vinyl carboxylates of formula

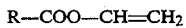

R—COO—CH=CH$_2$ in which R represents a monovalent and preferably aliphatic hydrocarbon group having 1 to 30 and preferably 1 to 21 carbon atoms. Among these preferred compounds, use is most frequently made of those from the group formed by copolymers of ethylene and vinyl carboxylate chosen from within the group constituted by vinyl acetate, vinyl propionate and vinyl butyrates. For example, reference can be made to ethylene-vinyl acetate copolymers and ethylene-vinyl propionate copolymers. Usually these copolymers contain 10 to 60% and preferably 15 to 50% by weight of ester.

In the preferred embodiment of the invention, the formulations also incorporate at least one constituent (C), chosen from within the group formed by paraffin crystal growth inhibiting products. Normally use is made of a constituent (C) chosen from within the group formed by alkyl polyacrylates, alkyl polymethacrylates, in which the alkyl group has 1 to 30 and preferably 4 to 24 carbon atoms, and copolymers formed from dialkyl fumarates, in which the alkyl groups have 1 to 30 carbon atoms, and vinyl carboxylates of formula

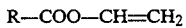

R—COO—CH=CH$_2$ in which R represents a monovalent and preferably aliphatic hydrocarbon group having 1 to 30 and preferably 1 to 21 carbon atoms. Among these compounds preference is given to the use of alkyl polyacrylates or alkyl polymethacrylates, in which the alkyl group has at least 6 carbon atoms and the copolymers formed from the dialkyl fumarates, in which the alkyl groups, which are the same or different, have at least 6 carbon atoms, and the vinyl carboxylates chosen from within the group formed by vinyl acetate, vinyl propionate and vinyl butyrates. Usually use is made of polymethacrylates and in particular polymethacrylates of long chain alcohols having e.g. at least 6 and often 10 to 24 carbon atoms. As examples of acrylates and methacrylates used, reference can be made to butyl, ethylhexyl, decyl, dodecyl, hexadecyl, octadecyl and eicosyl acrylates. Reference can also be made to acrylates and methacrylates of industrial alcohol fractions containing on average 12 carbon atoms (lauryl acrylate and methacrylate) or 18 carbon atoms (stearyl acrylate or methacrylate), as well as heavier alcohol fractions, which are rich in alcohols having 20 or 22 carbon atoms. As examples of such fractions, reference can be made to a fraction having, by weight, 54% C$_{12}$ alcohols, 24% C$_{14}$ alcohols, 10% C$_{16}$ alcohols and 12% C$_{18}$ alcohols and a fraction having, by weight, 8% C$_{18}$ alcohols, 67% C$_{20}$ alcohols and 25% C$_{22}$ alcohols. As examples of copolymers of dialkyl fumarates and vinyl carboxylates reference can be made to polymers formed from vinyl acetate and fumarate, in which the alkyl groups come from long chain alcohols e.g. having at least 6 carbon atoms. and e.g. those having 10 to 20 carbon atoms. The alkyl groups of these fumarates can come from industrial alcohol fractions, such as those referred to hereinbefore.

The formulations according to the invention are in particular usable as an additive having a good antisedimentation activity, a reduced filterability temperature limit and a reduced operability temperature limit, for a fuel containing paraffins based on hydrocarbons or a mixture of hydrocarbons and at least one oxygen compound, chosen from within the group formed by alcohols and ethers. Normally these formulations are added to the fuel so as to obtain a weight concentration of the additive composition in the fuel of 10 to 10,000, frequently 100 to 5,000 and preferably 100 to 2,000 ppm.

As examples of fuels which can contain at least one compound according to the present invention, reference can be made to gas oils or diesel fuels, such as e.g. those defined by Standard ASTM D-975. These fuels can also contain other additives, such as antifreeze additives, anticorrosion additives and additives more specifically of the detergent type.

In the formulations according to the present invention the weight ratio of constituent (A) to constituent (B) [(A)/(B)] is normally approximately 0.05:1 to approximately 5:1. This ratio is often approximately 0.05:1 to approximately 2:1 and preferably approximately 0.1:1 to approximately 2:1. When the formulation also incorporates a constituent (C) the weight ratio of constituent (B) to constituent (C) [(B)/(C)] is normally approximately 0.1:1 to approximately 5:1 and preferably approximately 0.2:1 to approximately 2:1. This ratio [(B)/(C)] is very often relatively close to 1:1.

The formulations according to the present invention can be directly added to the fuel by a simple mixing operation. However, it is often advantageous to introduce them in the form of "mother solutions" prepared beforehand in the solvents referred to hereinbefore. The "mother solutions" can e.g. contain 20 to 60% and most frequently approximately 50% by weight of additives.

The following examples illustrate, but in no way limit the scope of the invention.

EXAMPLE 1 a) First Stage

Into a 2 liter three-necked flask, immersed in an oil bath provided with a bar magnet stirrer, a thermometer, a dropping funnel and a Dean and Stark apparatus, are introduced 266 g of n-dodecenyl succinic anhydride (i.e. 1 mole) and the same weight of xylene. Addition slowly takes place using the dropping funnel of 61 g of aminoethanol (i.e. 1 mole) diluted by the same xylene quantity. Rapid heating to xylene reflux takes place, which is maintained for 3 hours. This is followed by the collection of 17.5 g of water and 309 g of product following the evaporation of the xylene. This product is analysed by infrared spectrometry and NMR of the proton. The IR spectrum contains large bands at 1400 and 1717 cm$^{-1}$ characteristic of the imide group and an intense band at 3450 cm$^{-1}$ characteristic of the hydroxyl group. The NMR spectrum has the expected peaks with the desired intensity, which corresponds to the aminoethanol dodecenyl succinimide.

b) Second Stage

Into a 2 liter three-necked flask are introduced 47.3 g of phosphoric anhydride (⅓ mole) suspended in the same weight of xylene. The imide-alcohol obtained in the first stage and diluted in the same weight of xylene is slowly added by means of the dropping funnel, under an argon atmosphere, in order to prevent hydration of the phosphoric anhydride. When the two reagents are completely dissolved at ambient temperature, slight heating takes place (to 60° C. in the oil bath) for 45 minutes. A homogeneous liquid product is obtained, which is analysed by infrared and NMR of the proton. The IR spectrum reveals the disappearance of the —OH band at 3450 cm$^{-1}$ and the appearance of a wide band at 1010 cm$^{-1}$ corresponding to the P-O-C vibration. The NMR spectrum of the proton makes it possible to see the chemical displacement of the protons of the phosphates at 9 ppm.

c) Third Stage

To the product of the second stage are slowly added by means of the dropping funnel, 521 g (i.e. 1 mole) of a secondary fatty amine fraction of formula R$^3$R$^4$NH corresponding to the fraction A of table 1, diluted by the same xylene weight. By slight heating at approximately 50° C. and stirring for 30 minutes, following evaporation of the xylene, a liquid is obtained which is solidified at ambient temperature and which is analysed by IR and NMR spectrometry. The IR spectrum is similar to the spectrum of the second stage product. On the NMR spectrum it is possible to see an increase in the number of CH$_2$ and CH$_3$ protons due to the protons of amines. Analysis of the NMR spectra of the phosphorus makes it possible to establish that only amine phosphates are formed with very small polyphosphate quantities. The product obtained, diluted to 50% by weight in xylene, is called additive 1.

EXAMPLE 2

The first and second stages of Example 1 are repeated replacing the n-dodecenyl succinic anhydride by tetrapropenyl succinic anhydride, using the same apparatus and the same reagent quantities. The product from the second stage is subdivided into two equal 178 g portions. To one of the portions are added 260 g (i.e. ½ mole) of the same secondary amine fraction as in the third stage of Example 1 and diluted by the same weight of xylene. The product obtained, diluted to 50% by weight in xylene, is called additive 2.

EXAMPLE 3

To the second portion of the product of the second stage of Example 2 (178 g) are added 300 g (½ mole) of a secondary fatty amine fraction of formula R$^3$R$^4$NH corresponding to fraction B of table 1, diluted by the same weight of xylene. The product obtained, diluted to 50% in xylene, is called additive 3.

EXAMPLES 4 TO 7

The first and second stages of Example 1 are repeated replacing the n-dodecenyl succinic anhydride by a polyisobutene succinic anhydride (PIBSA) (the determination of the anhydride functions of this product reveals that there is 0.74 anhydride function per kg) in the same apparatus with stoichiometric quantities of anhydride (1 mole) and aminoethanol (1 mole). The product from the second stage is subdivided into four equal portions:

- to the first portion is added ¼ mole of dibutyl amine diluted with xylene,
- to the second portion is added ¼ mole of a secondary fatty amine fraction of formula R$^3$R$^4$NH corresponding to fraction C of table 1,
- to the third portion is added ¼ mole of the secondary fatty amine fraction of formula R$^3$R$^4$NH corresponding to fraction A of table 1,
- to the fourth portion is added ¼ mole of the secondary fatty amine fraction of formula R$^3$R$^4$NH corresponding to fraction B of table 1.

The products obtained, diluted to 50% by weight in xylene, are called additives 4, 5, 6 and 7.

EXAMPLES 8 TO 12

The procedure described in Examples 4 to 7 is repeated replacing the polyisobutene succinic anhydride with 0.74 anhydride function per theoretical mole by a polyisobutene succinic anhydride with 1.23 anhydride function per kg. The product from the second stage is subdivided into five equal portions, four portions being treated by the same amines as in Examples 4 to 7. The fifth portion is treated by a primary amine with a branched C$_{18}$ to C$_{22}$ chain in place of the secondary fatty amines. The products obtained, diluted to 50% by weight in xylene, are called additives 8, 9, 10, 11 and 12.

EXAMPLE 13

The procedure described in Example 1 is repeated replacing the n-dodecenyl succinic anhydride by n-octadecenyl succinic anhydride. This gives a product which, diluted by the same weight of xylene, is called additive 13.

EXAMPLE 14

The procedure described in Example 1 is repeated replacing the aminoethanol by 6-amino-1-hexanol. The product obtained diluted by the same weight of xylene, is called additive 14.

EXAMPLE 15

The thus prepared additives were tested in the laboratory in formulations intended for the improvement of the cold behaviour of gas oils, in order to evaluate their antisedimentation activity with respect to paraffins. The sedimentation tests were performed in a chamber, whose temperature can be lowered to −30° C. All the tests were performed at −15° C. using 250 cm³ test tubes. The low temperature was maintained for 24 hours in a first test and 7 days in a second test. At the end of each of these tests a visual rating assessed the deposited sediment volumes of cloudy gas oil and clear or limpid gas oil.

The upper phase quality is determinative for the antisedimentation effectiveness of the additive. When the upper phase is cloudy, a large paraffin proportion has remained suspended. When this phase is clear, almost all the paraffins have been sedimented.

On now considering the sedimented paraffin quantity, the more the upper phase is dewaxed, the more the sedimented phase is dense, which makes it difficult to pump the gas oil. It is only possible to compare the sedimented paraffin quantities if they have an equivalent density, i.e. if the upper phases are of the same nature.

The tested formulations contain 100 ppm of additives 1 to 14 according to the invention.

Table II gives the characteristics of the gas oils used.
Table III gives the results of the sedimentation tests.

To the product from the second stage is added ¼ mole of a secondary fatty amine fraction of formula $R^3R^4NH$ corresponding to fraction C of table 1.

The constituent (B) is either the copolymer (B1) formed from ethylene and vinyl acetate containing 32% by weight vinyl acetate, of number average molecular weight, measured by tonometry, of 4900 and polydispersity number equal to 2.5, or the copolymer (B2) formed from ethylene and vinyl propionate containing 30% by weight vinyl propionate of number average molecular weight, measured by tonometry, of 5900 and a polydispersity number equal to 2.3. The constituent (C) is either copolymer (C1) formed from vinyl acetate and fumarate of an alcohol fraction containing, by weight, 30% $C_{12}$ alcohols, 27% $C_{14}$ alcohols, 14% $C_{16}$ alcohols, 18% $C_{18}$ alcohols and 11% $C_{20}$ alcohols, or compound (C2) consisting of a polymethacrylate of said same alcohol fraction of number average molecular weight, measured by tonometry, of 26100 and polydispersity number equal to 2.7. The copolymer (C1) has a number average molecular weight, measured by tonometry, of 16300 and a polydispersity number of 2.6. These formulations are added to the fuel in the form of a solution in xylene containing 50% by weight dry matter.

TABLE II

| Gas Oil No. | Distillation NF M07-002 | | | Density at 15° C. (kg/m³) | Paraffins wt. % | P.T. (°C.) | F.T.L. (°C.) | P.E. (°C.) |
|---|---|---|---|---|---|---|---|---|
| | P.I. (°C.) | P.F. (°C.) | % distilled at 300° C. | | | | | |
| I | 155 | 373 | 72 | 830 | 11 | −6 | −4 | −17 |
| II | 162 | 377 | 70 | 833 | 10 | −5 | −3 | −18 |

TABLE III

| Additive No. | Gas Oil I (Volume in cm³) | | | | | | Gas Oil II (Volume in cm³) | | | | | |
|---|---|---|---|---|---|---|---|---|---|---|---|---|
| | Clear | | Cloudy | | sediments | | Clear | | Cloudy | | Sediments | |
| | 1 d | 7 d | 1 d | 7 d | 1 d | 7 d | 1 d | 7 d | 1 d | 7 d | 1 d | 7 d |
| 1 | 0 | 0 | 250 | 250 | 0 | 0 | 0 | 0 | 250 | 250 | 0 | 0 |
| 2 | 0 | 0 | 250 | 250 | 0 | 0 | 0 | 0 | 220 | 210 | 30 | 40 |
| 3 | 0 | 215 | 250 | 35 | 0 | 0 | 0 | 0 | 250 | 250 | 0 | 0 |
| 4 | 0 | 0 | 250 | 250 | 0 | 0 | 5 | 80 | 245 | 170 | 0 | 0 |
| 5 | 0 | 0 | 250 | 250 | 0 | 0 | 6 | 15 | 244 | 235 | 0 | 0 |
| 6 | 0 | 0 | 250 | 250 | 0 | 0 | 0 | 0 | 250 | 250 | 0 | 0 |
| 7 | 0 | 0 | 250 | 250 | 0 | 0 | 0 | 110 | 250 | 140 | 0 | 0 |
| 8 | 0 | 0 | 250 | 250 | 0 | 0 | 0 | 90 | 250 | 160 | 0 | 0 |
| 9 | 10 | 50 | 240 | 200 | 0 | 0 | 0 | 110 | 250 | 140 | 0 | 0 |
| 10 | 0 | 0 | 250 | 250 | 0 | 0 | 0 | 0 | 250 | 250 | 0 | 0 |
| 11 | 5 | 60 | 245 | 190 | 0 | 0 | 0 | 150 | 250 | 100 | 0 | 0 |
| 12 | 0 | 0 | 250 | 250 | 0 | 0 | 0 | 0 | 250 | 250 | 0 | 0 |
| 13 | 0 | 0 | 250 | 250 | 0 | 0 | 0 | 0 | 250 | 250 | 0 | 0 |
| 14 | 0 | 0 | 250 | 250 | 0 | 0 | 0 | 0 | 250 | 250 | 0 | 0 |

EXAMPLE 16

Solutions are prepared in xylene of formulations incorporating different quantities by weight of constituents (A), (B) and (C) defined hereinafter. The constituents (A) used are:

(A1): additive 1 obtained in Example 1,
(A2): additive 2 obtained in Example 2,
(A3): an additive prepared according to the following procedure.

The first and second stages of Example 1 are repeated replacing the n-dodecenyl succinic anhydride by a polyisobutene succinic anhydride (PIBSA) (the determination of the anhydride functions of this product reveals that there is 0.74 anhydride function per kg) using the same apparatus and with stoichiometric quantities of anhydride (1 mole) and aminoethanol (1 mole).

The concentration of each of the compounds in the fuel are defined in each case. The thus prepared formulations were tested in the laboratory in order to evaluate their activity on the cold behaviour of gas oils. Tests were carried out to evaluate their antisedimentation, crystal growth inhibition and operability activities.

EXAMPLE 17

The sedimentation tests were carried out in the manner described in Example 15.

The tested formulations contain various quantities of compounds A, B and C. Comparative tests were also carried out on gas oils to which no additives had been added and on gas oils only containing one of these compounds.

Table IV gives the results of the sedimentation tests.

TABLE IV

| formulation | mg | Gas Oil I (Volume in cm³) | | | | | | Gas Oil II (Volume in cm³) | | | | | |
|---|---|---|---|---|---|---|---|---|---|---|---|---|---|
| | | Clear | | Cloudy | | Sediments | | Clear | | Cloudy | | Sediments | |
| | | 1 d | 7 d | 1 d | 7 d | 1 d | 7 d | 1 d | 7 d | 1 d | 7 d | 1 d | 7 d |
| B1* | 750 | 195 | 210 | 0 | 0 | 55 | 40 | 174 | 195 | 0 | 0 | 76 | 55 |
| B2* | 750 | 190 | 215 | 0 | 0 | 60 | 45 | 160 | 178 | 0 | 0 | 90 | 72 |
| C1* | 750 | 0 | 0 | 235 | 220 | 15 | 30 | 0 | 0 | 230 | 228 | 20 | 22 |
| C2* | 750 | 200 | 205 | 0 | 0 | 50 | 45 | 12 | 115 | 238 | 0 | 0 | 135 |
| A1* | 750 | 0 | 0 | 250 | 250 | 0 | 0 | 0 | 0 | 250 | 250 | 0 | 0 |
| A2* | 750 | 0 | 0 | 250 | 250 | 0 | 0 | 0 | 0 | 220 | 210 | 30 | 40 |
| A3* | 750 | 0 | 0 | 250 | 250 | 0 | 0 | 0 | 0 | 250 | 250 | 0 | 0 |
| B1 C2 | 375 375* | 0 | 210 | 220 | 0 | 30 | 40 | 0 | 0 | 230 | 220 | 20 | 30 |
| A1 B2 | 375 375 | 0 | 200 | 180 | 0 | 70 | 50 | 0 | 200 | 175 | 0 | 75 | 50 |
| A1 B2 | 375 375 | 0 | 0 | 178 | 196 | 72 | 54 | 0 | 0 | 184 | 202 | 66 | 48 |
| A2 B1 | 375 375 | 0 | 0 | 187 | 202 | 63 | 48 | 0 | 202 | 180 | 0 | 70 | 48 |
| A3 B1 | 375 375 | 0 | 0 | 177 | 200 | 73 | 50 | 0 | 0 | 178 | 195 | 72 | 55 |
| A1 B1 C2 | 250 250 250 | 0 | 0 | 248 | 245 | 2 | 5 | 0 | 0 | 240 | 200 | 10 | 50 |
| A2 B1 C2 | 250 250 250 | 0 | 0 | 248 | 240 | 2 | 10 | 0 | 0 | 242 | 240 | 8 | 10 |
| A3 B1 C2 | 250 250 250 | 0 | 0 | 250 | 250 | 0 | 0 | 0 | 0 | 250 | 250 | 0 | 0 |
| A1 B1 C2 | 100 250 400 | 0 | 0 | 248 | 245 | 2 | 5 | 0 | 0 | 250 | 250 | 0 | 0 |
| A1 B1 C2 | 150 180 420 | 0 | 0 | 248 | 240 | 2 | 10 | 0 | 0 | 250 | 250 | 0 | 0 |
| A2 B1 C2 | 100 250 400 | 0 | 0 | 248 | 240 | 2 | 10 | 0 | 0 | 250 | 250 | 0 | 0 |
| A2 B1 C2 | 180 150 450 | 0 | 0 | 248 | 240 | 2 | 10 | 0 | 0 | 250 | 250 | 0 | 0 |

*Comparison

EXAMPLE 18

Use is made of gas oil No. 1, whose characteristics are given in table II for evaluating the action of formulations according to the invention and comparison formulations on the inhibition of paraffin crystal growth using a filtration method employing 25 mm filters. The filtration pressure is fixed at 660 mbar. The test was carried out in a chamber cooled to 6° C. per hour. The flow rate curves make it possible to evaluate the tendency to clogging of the filter by paraffins. The tested formulations were the same as those used for the sedimentation tests, but the relative proportions of the constituents were varied. Table V gives the results obtained with regards to the filterability temperature limit.

TABLE V

| Compound A | mg | Compound B | mg | Compound C | mg | F.T.L. °C.** |
|---|---|---|---|---|---|---|
| A1 | 120 | B1 | 350 | C2 | 280 | −16 |
| A1 | 100 | B1 | 250 | C2 | 400 | −16 |
| A2 | 120 | B1 | 350 | C2 | 280 | −20 |
| A | 0 | B | 0 | C | 0 | *−5 |
| A1 | 750 | B | 0 | C | 0 | *−9 |
| A2 | 750 | B | 0 | C | 0 | *−9 |
| A | 0 | B1 | 750 | C | 0 | *−14 |
| A | 0 | B | 0 | C2 | 750 | *−23 |
| A | 0 | B1 | 375 | C2 | 375 | *−13 |
| A2 | 375 | B1 | 375 | C2 | 0 | −13 |
| A2 | 375 | B | 0 | C2 | 375 | *−23 |

*Comparison
**F.T.L. is Filterability temperature limit.

EXAMPLE 19

Use is made of gas oil No. 1, whose characteristics are given in table II for evaluating the action of the formulations according to the invention and comparison formulations on the operability of the thus formulated fuels. Operability was evaluated on a Renault 21 diesel car supply circuit, in a cold chamber cooled 2° C. per hour and kept for 5 hours at the test temperature.

Table VI gives the operability temperature limit results obtained.

TABLE VI

| Compound A | mg | Compound B | mg | Compound C | mg | O.T.L. °C.** |
|---|---|---|---|---|---|---|
| A2 | 120 | B1 | 350 | C2 | 280 | −10 |
| A2 | 250 | B1 | 250 | C2 | 250 | −12 |
| A3 | 250 | B1 | 250 | C2 | 250 | −11 |
| A | 0 | B | 0 | C | 0 | *−6 |
| A2 | 750 | B | 0 | C | 0 | *−7 |
| A | 0 | B1 | 750 | C | 0 | *−8 |
| A | 0 | B | 0 | C2 | 750 | *−8 |
| A | 0 | B1 | 375 | C2 | 375 | *−7 |
| A2 | 375 | B1 | 375 | C2 | 0 | −9 |
| A2 | 375 | B | 0 | C2 | 375 | *−8 |

*Comparison
**O.T.L. Operability temperature limit

All these tests show that the formulations according to the invention make it possible to obtain an excellent compromise between the various selection criteria for a fuel to which additives have been added for its use on a vehicle. The preferred three-constituent formulations according to the present invention thus make it possible to obtain a filterability temperature limit and an operability temperature limit of a relatively low level, whilst bringing about a maximum paraffin sedimentation limitation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents, and publications, cited herein, and of corresponding French application Nos. 92/12 227 and 92/15 441, filed Oct. 9, 1992, and Dec. 18, 1992, respectively, are hereby incorporated by reference.

We claim:

1. An amine phosphate incorporating a terminal imide cycle, results from the reaction, under amine salt formation conditions, of at least one phosphate complying with the general formula (I):

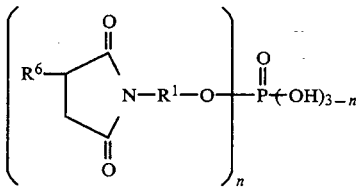

in which n is equal to 1 or 2, $R^1$ is a divalent hydrocarbon group having 1 to 32 carbon atoms, $R^6$ stands for a hydrogen atom or a hydrocarbon group normally having 1 to 200 carbon atoms, with at least one amine complying with one of the general formulas (II) or (III):

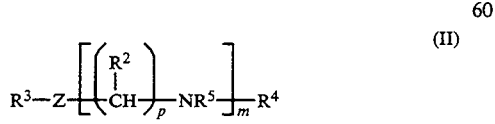 (II)

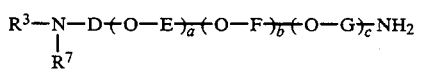 (III)

in which $R^3$, $R^4$ and $R^5$, which can be the same or different in each case represent a hydrogen atom or a hydrocarbon group having 1 to 60 carbon atoms, Z is chosen from among the groups —O— and —$NR^7$—, in which $R^7$ stands for a hydrogen atom or a hydrocarbon group having 1 to 60 carbon atoms, in which $R^3$ and $R^7$ can form together with the nitrogen atom to which they are linked a heterocycle, each of the $R^2$ independently representing a hydrogen atom or a hydrocarbon group having 1 to 4 carbon atoms, when Z is —$NR^7$—, p is an integer equal to or higher than 2 and m is zero or an integer from 1 to 10, when Z is —O—, p is an integer equal to or higher than 1 and m is an integer from 1 to 10, D, E, F and G, which are the same or different, in each case represent a divalent hydrocarbon group having 2 to 6 carbon atoms, a is an integer from 1 to 60, b and c, which are the same or different, are in each case zero or an integer from 1 to 50 and the sum a+b+c is an integer from 1 to 60.

2. A phosphate of the general formula (I):

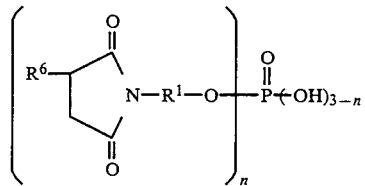

in which n, $R^1$ and $R^6$ have the definitions given in claim 1.

3. A process for the preparation of an amine phosphate according to claim 1, by stages a), b) and c) given hereinafter:

a) reaction takes place of at least one aminoalcohol of formula HO—$R^1$—$NH_2$ with at least one succinic derivative at a temperature of approximately 30° C. to approximately 250° C. under conditions for the formation of the imide cycle and for the elimination of the volatile products formed, b) the imide-alcohol solution obtained in stage a) or the imide-alcohol obtained in stage a) diluted in a liquid is progressively contacted with a suspension of phosphoric anhydride in a liquid phosphate formation conditions, c) to the liquid containing at least one phosphate of general formula (I), obtained in stage b), is slowly added at least one amine of general formula (II) and/or (III) under amine salt formation conditions.

4. A fuel composition, containing by weight, a major proportion of an engine fuel containing paraffins and a minor proportion, sufficient for slowing down the sedimentation of these paraffins during the cooling of these compositions, of at least one amine phosphate according to claim 1.

5. A composition according to claim 4 comprising 10 to 10,000 g/t of at least one amine phosphate.

6. An additive formulation for fuels containing paraffins, comprising at least one constituent (A) consisting of at least amine phosphate containing a terminal imide cycle as defined in claim 1 and at least one constituent (B) consisting of at least one paraffin germination additive.

7. A formulation according to claim 6, wherein the constituent (B) is chosen from within the group formed by copolymers of lower olefins having 2 to 12 carbon atoms, and-vinyl carboxylates of formula

R—COO—CH=CH$_2$ in which R represents a monovalent hydrocarbon group having 1 to 30 carbon atoms.

8. A formulation according to claim 6, wherein the constituent (B) is chosen from within the group formed by copolymers of ethylene and vinyl carboxylate chosen from within the group formed by vinyl acetate, vinyl propionate and vinyl butyrates.

9. A formulation according to claim 6, further comprising at least one constituent (C) chosen from within the group formed by paraffin crystal-growth-inhibiting products.

10. A formulation according to claim 9, wherein the constituent (C) is chosen from within the group formed by alkyl polyacrylates, alkyl polymethacrylates, in which the alkyl group has 1 to 30 carbon atoms, and copolymers formed from dialkyl fumarates, in which the alkyl groups have 1 to 30 carbon atoms, and vinyl carboxylates of formula

R—COO—CH=CH$_2$ in which R represents a monovalent hydrocarbon group having 1 to 30 carbon atoms.

11. A formulation according to claim 9, wherein the constituent (C) is chosen from within the group formed by alkyl polyacrylates, alkyl polymethacrylates, in which the alkyl group has at least 6 carbon atoms and copolymers formed from dialkyl fumarates, in which the alkyl groups have at least 6 carbon atoms, and vinyl carboxylates chosen from within the group formed by vinyl acetate, vinyl propionate and vinyl butyrates.

12. A fuel composition incorporating, by weight, a major proportion of an engine fuel containing paraffins and a minor proportion of at least one additive formulation according to claim 6.

13. A composition according to claim 12 comprising 10 to 10,000 ppm by weight of the additive formulation in the fuel.

14. A composition according to claim 12, wherein said formulation comprises the constituents (A) and (B) in a weight ratio (A)/(B) of approximately 0.05:1 to approximately 5:1.

15. A composition according to claim 11, wherein said formulation also comprises a constituent (C) in a weight quantity such that the weight ratio (B)/(C) is approximately 0.1:1 to approximately 5:1.

16. A process for the preparation of a phosphate according to claim 2, comprising:
(a) reacting at least one aminoalcohol of formula HO—R$^1$—NH$_2$ with at least one succinic derivative at a temperature of approximately 30° C. to approximately 250° C. under conditions for the formation of the imide cycle and for the elimination of the volatile products formed, and
(b) progressively contacting the resultant imide-alcohol solution obtained in stage (a) or the imide-alcohol obtained in stage (a) diluted in a liquid, with a suspension of phosphoric anhydride in a liquid under phosphate formation conditions.

17. A process according to claim 3 wherein the imide-alcohol is diluted in a liquid, and the phosphoric anhydride is suspended in the same liquid.

18. A process according to claim 17, wherein the at least one amine is diluted in a liquid which is the same as that used in stage (b).

19. A process according to claim 16 wherein the imide-alcohol is diluted in a liquid, and the phosphoric anhydride is suspended in the same liquid.

20. A formulation according to claim 7, wherein said lower olefins contain 2–4 carbon atoms.

21. A process according to claim 20, wherein the monovalent hydrocarbon group is aliphatic and contains 1–21 carbon atoms.

22. A formulation according to claim 10, wherein said alkyl group has 4–24 carbon atoms.

23. A formulation according to claim 22, wherein said monovalent hydrocarbon group is aliphatic and contains 1–21 carbon atoms.

* * * * *